(12) United States Patent
Kim

(10) Patent No.: US 6,398,742 B1
(45) Date of Patent: Jun. 4, 2002

(54) URINE DISCHARGE APPARATUS FOR FEMALE

(76) Inventor: Kyoung Hun Kim, 17-26, Dongkwang-dong 2-ga, Joong-ku, Pusan 600-002 (KR)

( * ) Notice: Subject to any disclaimer, the term of this patent is extended or adjusted under 35 U.S.C. 154(b) by 0 days.

(21) Appl. No.: 09/636,672

(22) Filed: Aug. 11, 2000

Related U.S. Application Data

(63) Continuation of application No. PCT/KR99/00074, filed on Feb. 12, 1999.

(30) Foreign Application Priority Data

Feb. 13, 1998 (KR) .............................................. 98-4280
Jan. 27, 1999 (KR) .............................................. 99-2595

(51) Int. Cl.[7] .......................... A61B 5/00; B65D 81/00
(52) U.S. Cl. ...................... 600/574; 604/329; 4/144.3
(58) Field of Search .............................. 600/573, 574, 600/578, 579; 604/319, 320, 329, 356; 4/144.1, 144.2, 144.3, 301, 450, 452, 454, 455, 456

(56) References Cited

U.S. PATENT DOCUMENTS

| | | | | |
|---|---|---|---|---|
| 4,345,341 A | * | 8/1982 | Saito ............................. | 4/301 |
| 4,366,818 A | * | 1/1983 | Izumi ......................... | 604/350 |
| 4,631,061 A | * | 12/1986 | Martin ........................ | 604/329 |
| 4,747,166 A | * | 5/1988 | Kuntz ......................... | 4/144.1 |
| 5,049,144 A | * | 9/1991 | Payton ....................... | 604/329 |
| 5,195,997 A | * | 3/1993 | Carns .......................... | 604/347 |
| 5,454,798 A | * | 10/1995 | Kubalak et al. ............. | 604/328 |
| 5,678,564 A | * | 10/1997 | Lawrence et al. .......... | 600/574 |
| 5,913,832 A | * | 6/1999 | Sagalovich et al. ......... | 600/573 |
| 6,183,454 B1 | * | 2/2001 | Levine et al. ............... | 604/329 |

* cited by examiner

Primary Examiner—Kevin Shaver
Assistant Examiner—Charles Marmor, II
(74) Attorney, Agent, or Firm—Akin, Gump, Strauss, Hauer & Feld, L.L.P.

(57) ABSTRACT

The present invention provides a urine discharge apparatus for a female comprising a collection member (6) in the shape of bucket. A disposable pack (7) is inserted in the collection member (6). The disposable pack (7) has a circumferential flange (71) in the side wall adapted for contacting the perinaeum neum and a test paper (16) for detection of disease and pregnancy. A pump member (3) is connected to the collection member (6) by a hinge pin (14) and has a pump (5) in the interior thereof. The pump (5) is open to the collection member (6) so that the pump (5) sucks in the urine collected in collection member (6) and discharges the urine into the outlet (53) thereof. A driving member (2) operates the pump (5) by electric power supplied from a battery contained in the driving member (2). The pump member (3) and the driving member (2) for operating the pump (5) may be designed independently or incorporated into the unitary body (1).

35 Claims, 8 Drawing Sheets

URINE DISCHARGE APPARATUS FOR FEMALE

CROSS-REFERENCE TO RELATED APPLICATIONS

This application is a continuation of International Application PCT/KR99/00074, filed Feb. 12, 1999, the disclosure of which is incorporated herein by reference.

BACKGROUND OF THE INVENTION

The present invention relates to a urine discharge apparatus for a female, and particularly to a urine discharge apparatus providing the advantage that urine collected in a disposable pack by a collection member is discharged without detention by use of a small pump, further having the advantage that it is convenient to carry and store due to its small volume when folded.

Generally, urination of a female is different from that of a male, having the problem that a female must excessively expose her body to maintain a sitting position with her trousers taken off. In order to hide her exposed body, a female usually uses a toilet seat in a closed space. However, in the case that a public toilet is not available, urination of a female is inevitably accompanied by an excessive exposure of her body which imposes a burden on her and may even evoke a gender complex.

In order to minimize the exposure of body and overcome the gender complex, a "female urine discharge device" disclosed by publication of Laid-open Korea Patent Application 95-5332 was proposed.

The proposed device has a funnel-shaped hemisphere and protects against leakage of urine by a contact portion of the hemisphere, whose rim is made of soft material, a sawtoothed anti-back current means in the interior surface for preventing back current of urine after urination and a outlet pipe that is wrinkled.

While not in use, this device is kept in a pocket placed in the user's underwear in a manner such that the outlet pipe is attached to the underwear and folded upwardly.

However, because the contact portion is easily separated from the hemisphere when the device is taken out of the pocket for use, the device is very inconvenient. Further, because the urethra of a female is located at a lower place of the body, the underwear may be spoiled by the spreading of urine. Thus, urine is not collected in an outlet pipe protruding forward. Accordingly, repeated use of the device is impossible and cumbersome since a female must always wear the device during her activity In addition, since females usually urinate 7 or 8 times a day and deject 1 or 2 times a day, females use toilet seats more frequently than males and thus public toilets may become overcrowded.

Accordingly, infection through a toilet seat may occur more frequently.

BRIEF SUMMARY OF THE INVENTION

The present invention is proposed to solve the above mentioned problem. The object of the invention is to provide a "urine discharge apparatus for a female" that females carry at normal times, attaching the apparatus to the perinaeum neum prior to urination. The apparatus is also convenient to carry and store and also makes it possible to examine the amount of urine, and therefore also has a medical use for early detection of disease.

After urination, the urine collected in the collection member is discharged outside the device without detention by the pump.

The present invention also provides a urine discharge apparatus for a female whose driving member, pump member and collection member cooperate with one another by a hinge coupling so as to control the flow of urine discharged.

Another object of the present invention is to provide a urine discharge apparatus for a female that uses a disposable pack for sanitary urination The disposable pack is also useable for medical examination and pregnancy diagnosis.

Another object of the present invention is to provide a urine discharge apparatus for a female that enables a bedridden patient to urinate by oneself or with help of a nurse while in the bed.

BRIEF DESCRIPTION OF THE SEVERAL VIEWS OF THE DRAWINGS

The foregoing summary, as well as the following detailed description of preferred embodiments of the invention, will be better understood when read in conjunction with the appended drawings. For the purpose of illustrating the invention, there is shown in the drawings embodiments which are presently preferred. It should be understood, however, that the invention is not limited to the precise arrangements and instrumentalities shown.

In the drawings.

The primary reference numbers correspond to the following elements:

| [0032] | 1:body | 2:driving member |
|---|---|---|
| [0033] | 3:pump member | 4:battery case |
| [0034] | 5:pump | 6:collection member |
| [0035] | 7:disposable pack | 9:switch |
| [0036] | 12:door | 13:discharge hose |
| [0037] | 13:auxiliary hose | 15:discharge pipe |
| [0038] | 16:test paper | 41, 42:receptacle |
| [0039] | 51:impeller | 52:inlet |
| [0040] | 53:outlet | 62:magnet |
| [0041] | 81:groove | 82:rear wall |
| [0042] | 83:hose clip | 831:blade portion |
| [0043] | 85:bottom | 87:display |
| [0044] | 88:holder | 131:introduction hose |

DETAILED DESCRIPTION OF THE INVENTION

According to the present invention, a urine discharge apparatus for a female comprises a bode divided into a driving member and a pump member. The members cooperate with one another by a hinge means. A battery case is rotatably connected to a holding clip mounted on the driving member to receive a battery during rotation of the battery case to supply power to the device. A switch is located on the outer surface of the driving member to switch the electric power on and off. A door is incorporated in the driving member and to open and close an entrance to the battery case by a spring therein. A pump is incorporated in the pump member and has an impeller inside thereof with an inlet and an outlet for urine passage at both sides of the pump. A collection member is connected to one side of the pump member by a hinge means to collect urine. A discharge pipe is connected to the midpoint of the hinge means coupling the pump member and the collection member to introduce the urine collected in the collection member to the inlet of the pump. A discharge hose has one end connected to the outlet of the pump and the other end connected to the passage formed in the lower portion of the driving member such that the urine can be discharged outside through the discharge hose.

The present invention will be described in further detail with reference to the accompanying drawings.

Figure 1:
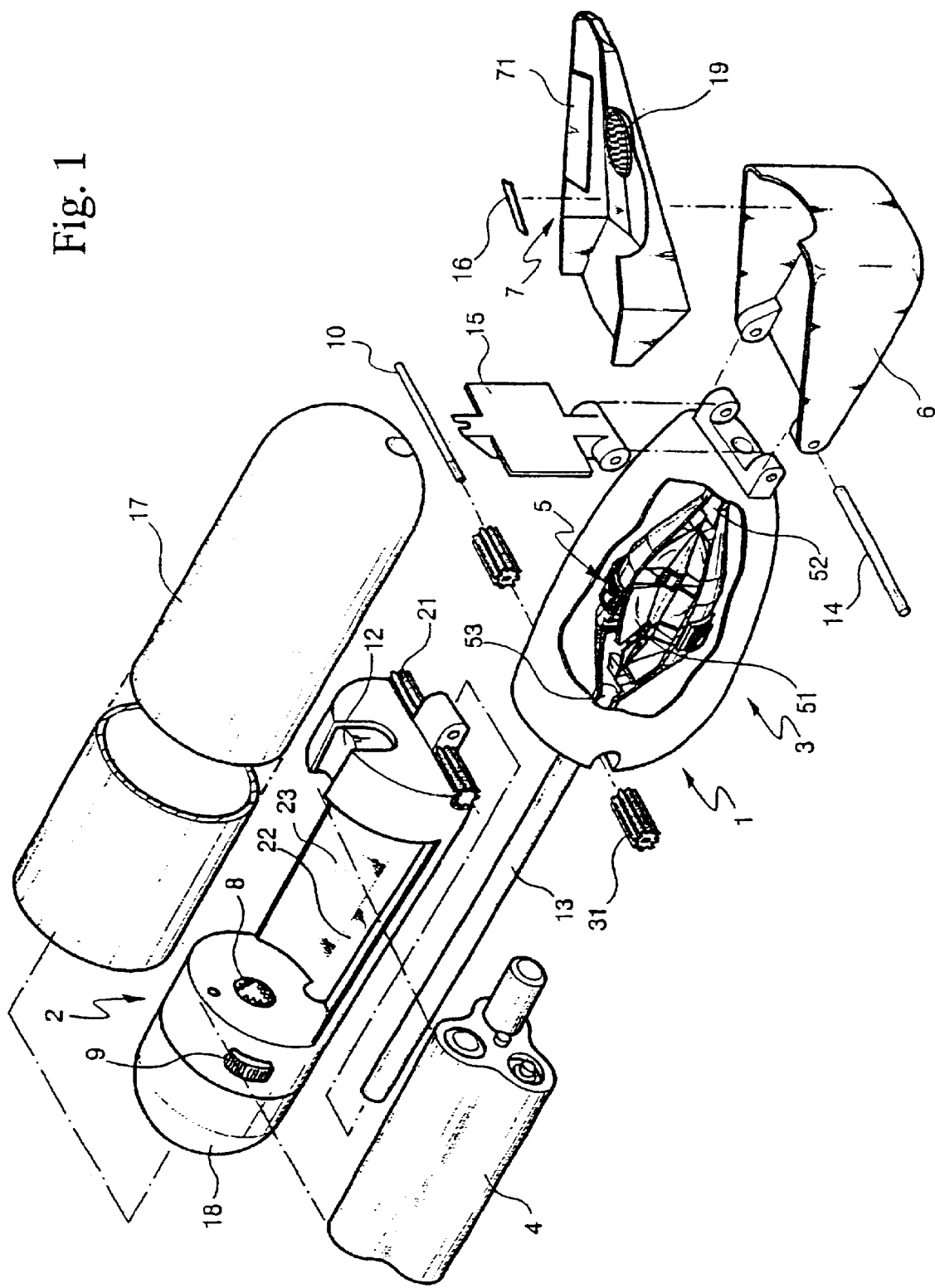
FIG. 1 is an exploded perspective view showing the separated urine discharge apparatus according to one embodiment of the present invention.
Figure 2:
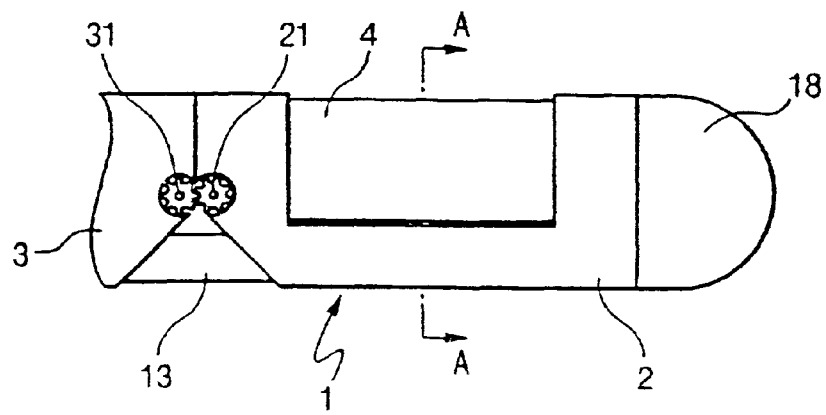
FIG. 2 is a side view showing a portion of the urine discharge apparatus according to one embodiment of the present invention.
Figure 3:
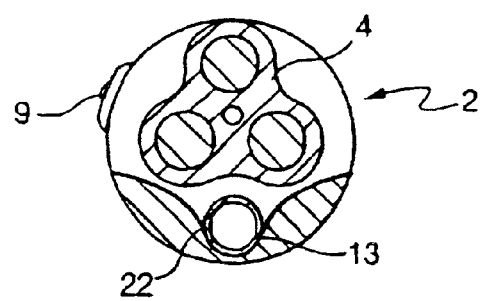
FIG. 3 is a cross-sectional view taken from line A—A of FIG. 2.

Referring to FIG. 1, a body 1 is divided into the driving member 2 and the pump member 3. The members 2 and 3 are connected to each other by a hinge pin 10 in a manner such that a gear 21 engages with a gear 31.

The driving member 2 of the body 1 has a space 23 for carrying the battery case 4. The holding clip 8 is provided in the center of both sides of the space 23 so as to restrict rotation of the battery case 4.

Figure 4:
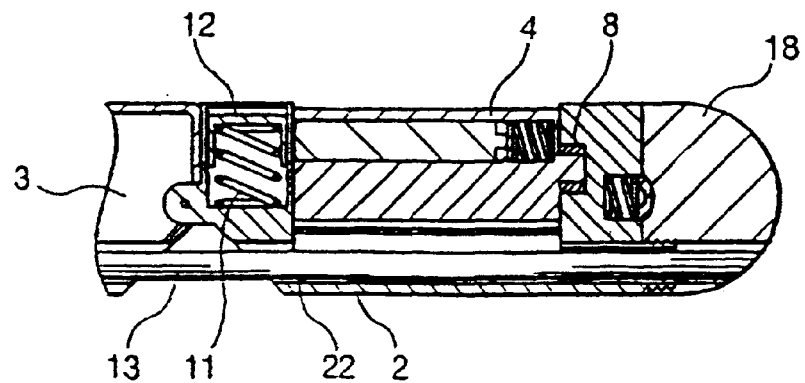
FIG. 4 is a longitudinal sectional view of FIG. 2.

The switch 9 for switching electric power on and off is provided on the outer surface of the driving member 2, but need not be located on the right side as shown. For example, the switch 9 may be located on the left side depending on the user's preferences so that user may operate the switch 9 with only a thumb. A door 12 which opens and closes the entrance of the battery case 4 by a spring 11 (see FIG. 4) is provided on the side of the space 23 opposite the switch 9. A through passage 22 is formed in the bottom of the driving member 2, and a discharge hose 13 is inserted into the through passage 22 and outward from the end of the driving member 2.

The battery case 4 preferably contains three 1.5 volt batteries, and is fitted in the holding clip 8 for restricting the battery case 4 from movement. A positive pole of the batteries is connected to the switch 9 and a negative pole to the pump 5 in the customary way. A rechargeable cell may be used instead of batteries.

The switch 9 operates the pump by connecting electric power of the batteries to the pump 5, and may be replaced by an adjustable resistance switch if more specialized control of rotation of the pump 5 is necessary.

The pump member 3 of the body 1 has a space for containing a small pump 5, and is connected to collection member 6 by means of a hinge pin 14. The collection member 6 is folded upwardly for storage and carrying. The collection member 6 may be unfolded to a predetermined angle when used. The pump 5 has the discharge pipe 15 and the discharge hose 13 at opposite ends.

The pump 5 is incorporated in the pump member 3 of the body 1 and contains an impeller 51 inside thereof. The impeller 51 is rotated by electric power supplied upon activation of the switch 9 to discharge urine. The pump 5 includes an inlet 52 connecting to the discharge pipe 15 on the side with the collection member 6, and an outlet 53 connecting to the discharge hose 13 on the opposite side of the pump 5. The pump 5 is not limiting and any typical pump suitable for moving urine may be used.

The discharge pipe 15 is located in the middle of the hinge means connecting the pump member 3 to the collection member 6 and can rotate independently about the pin 14. A flange on both sides of the discharge pipe 15 contacts completely with the surface of the collection member 6, and the discharge pipe 15 provides a passage for introducing the urine collected by the collection member 6 to inlet 52 of the pump 5.

Figure 8:
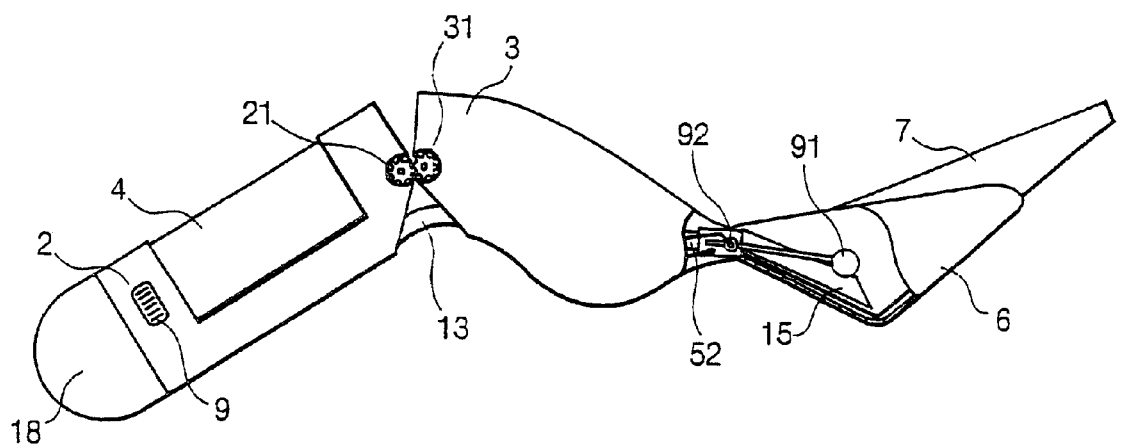
FIG. 8 is a modification of one embodiment, a partly sectional side view showing with an additional float-type switch for applying electric power provided.

As shown in FIG. 8, a floating type switch 92 may be additionally provided so as to connect in parallel a floater 91 and the switch 9 of the driving member 2 to the pump 5. When the floater 91 is raised from the surface of the collection member 6 upon collection of urine in the collection member 6, the floater 91 triggers the floating switch 92, thereby automatically driving the pump 5. This operation makes it possible to discharge urine independently of the switch 9 of the driving member 2.

A disposable pack 7 mounted on the collection member 6 is sold and stored in a folded condition. When used, the disposable pack 7 is unfolded to expose space for collecting urine. The disposable pack 7 is attached to the perinaeum neum, and includes a flange 71, provided longitudinally at both side walls, to prevent the urine discharged from the urethra from leaking, thus making collection of the urine easier. Additionally, a non-woven fabric 19 may be attached on the bottom of the disposable pack 7 to help absorb and prevent the spread of urine. Further, test paper 16 may be attached to the inside of the disposable pack 7 in order that the user, if necessary, may test for the presence of a proteinuira, haematouria, glycosuria or pregnancy.

The cover 17 is preferably made of resin or fabric and may be used to wrap the driving member 2 of the body 1 and pump member 3 for protection and/or to provide an aesthetically pleasing appearance. A cap 18 is connected to the top end of driving member 2 of the body 1.

Figure 7:
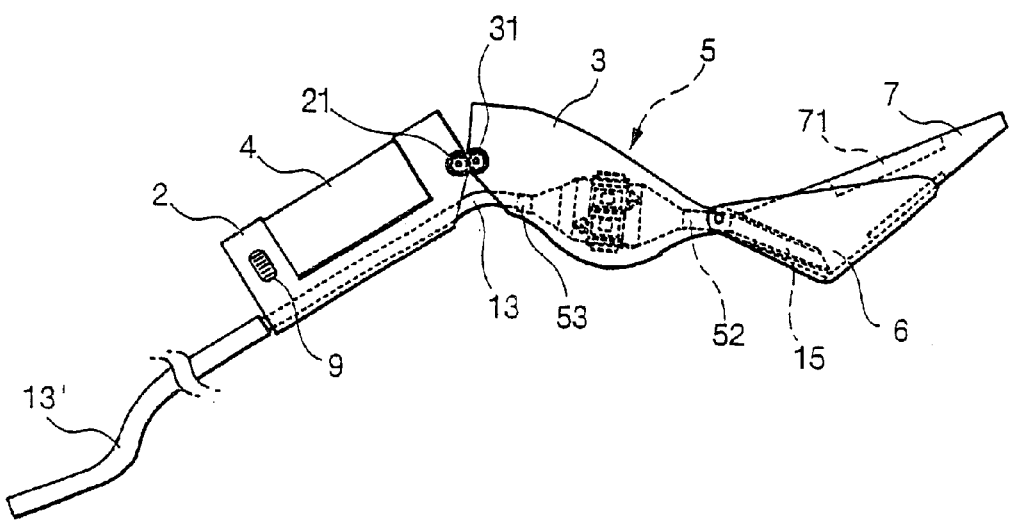
FIG. 7 is a side view showing a condition where an auxiliary hose is connected to the end of the discharge hose according to one embodiment of the present invention.

As shown in FIG. 7, an auxiliary hose 13' may be connected to the top end of the discharge hose 13 protruding outward from the driving member 2 to ensure that a bedridden patient can urinate in bed with the help of a nurse or by oneself, thus enabling the discharged urine to be easily collected in a separate drain or urinal.

The function of the above described urine discharge apparatus will now be described.

After the entrance of the battery case 4 is opened by lowering the door 12 of the driving member 2, the battery case 4 receives a battery and is then rotated repeatedly about a third of one turn until all batteries have been loaded. The collection member 6 is attached to the perinaeum neum after the discharge pipe 15 contacts the surface of the collection member 6, while the, driving member 2 and the pump member 3 are adapted to convenient angles for urination. For urination of a male, the driving member 2, the pump member 3 and the collection member 6 are adjusted to the same angle. The pump 5 is turned on simultaneously with urination or right before urination begins. The urine discharged from the urethra is introduced to the discharge pipe 15 from the collection member 6 by a sucking action of the pump 5 as soon as urine is collected in the collection member 6, and continuously flows from the inlet 52 of the pump 5 through impeller 51 to the outlet 53, and is finally discharged outward by operation of the pump 5 through the discharge hose 13.

After the urine collected in the collection member 6 is completely discharged, the operation of the pump 5 ceases by turning the switch 9 off. This completes an operating cycle of the urine discharge apparatus, and the apparatus may be folded for carrying or storage.

Figure 5:
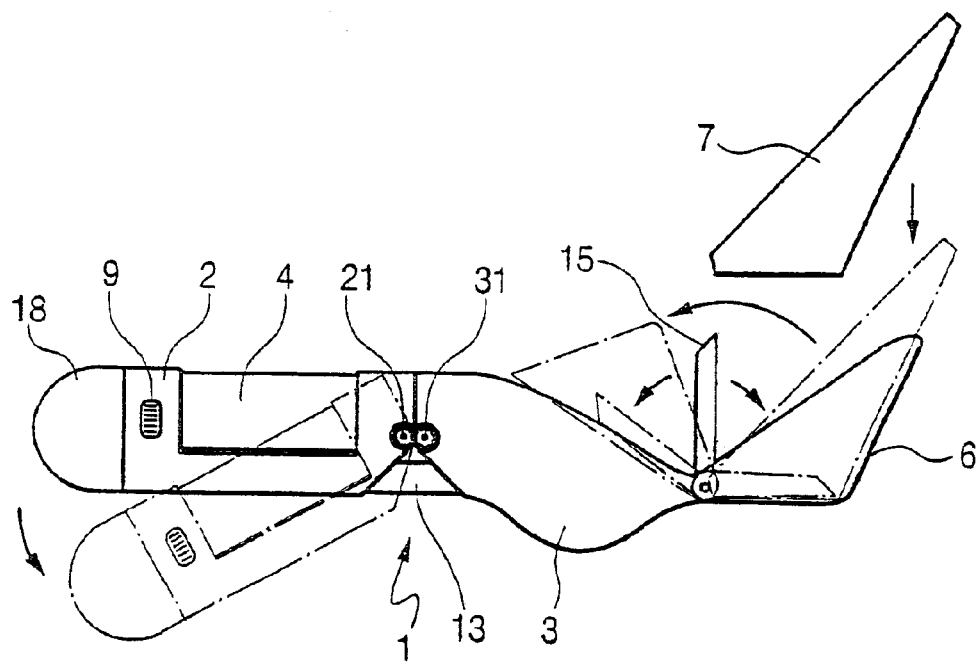
FIG. 5 is a side view showing an operational condition of the urine discharge apparatus according to one embodiment of the present invention.
Figure 6:
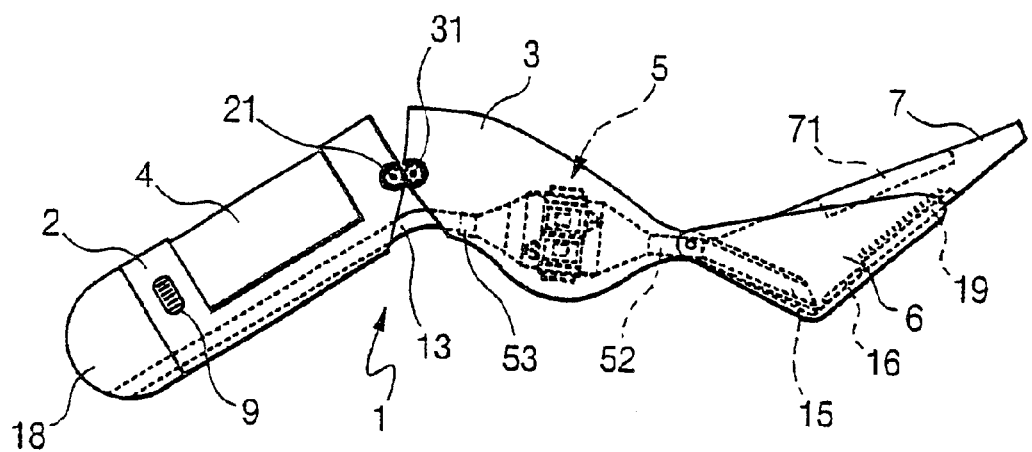
FIG. 6 is a side view showing a use condition of the urine discharge apparatus according to one embodiment of the present invention.

In the case that disposable pack 7 is used as shown in FIGS. 5 and 6, the function of the apparatus is the same as described above except that the disposable pack 7 is compressed by the discharge pipe 15. The use of the disposable pack 7 may ensure more sanitary urination since the urine is absorbed in the non-woven fabric 19 without leakage, and the flange 71 extending longitudinally in the side wall of the disposable pack 7 also effectively helps prevent spread or leakage of the urine. The test paper 16 attached to inside of the disposable pack 7 enables the user to easily check various health indexes.

Alternatively, when a bedridden patient uses the device to urinate in bed with help of a nurse or for oneself, the auxiliary hose 13' as shown in FIG. 7 may be connected to the top end of the discharge hose 13 protruding outward from the through passage 22 of the driving member 2 after a cap coupled with the top end of the driving member 2 is removed. Thus the discharged urine can be easily collected in another drain or urinal.

FIGS. 9–14 show another embodiment of the urine discharge apparatus according to the present invention. This alternate embodiment has a structure such that the pump member 3 and the driving member 2 are incorporated together into the body 1 to have a unitary shape.

In this embodiment, collection member 6 is in the form of a hemi-cone with a spherical base and is connected to both sides of the rear wall 82 of the body 1 by hinge pin 14'. The body 1 is the same shape as the collection member 6 so that the body 1 can rotate to be received into the collection member 6. A pump 5 having an inlet 52 and an outlet 53 is arranged longitudinally and an introduction hose 131 is connected to the inlet 52 and extends to and opens into the interior of the collection member 6. A discharge hose 13 connected to the outlet 53 of the pump 5 is arranged so as to discharge the urine outward from the device. A groove 81 is formed it a central line of the rear wall 82 of the body 1 so as to contain the introduction hose 131. A switch 9 connecting the pump 5 with electric power is mounted on the outside of the body 1. Receptacles 41 and 42 having doors 121 and 122 are both formed at the interior of the rear wall 82 so that the receptacles 41 and 42 each receive a battery.

A hose clip 83 having a blade portion 831 on both sides is provided to hold the introduction hose 131. Magnets 62 are attached to a front wall 61 of the collection member 6 so that the hose clip 83 may be secured completely to the front wall 61 by means of the magnets 62. The hose clip 83 has a guide portion 832 folded at an angle on both sides of the blade portion 831 so that the disposable pack 7 may be unfolded completely in accordance with the shape of the collection member 6, thus enabling the collection member 6, including the disposable pack 7, to collect the urine entirely.

A display 87 (FIG. 14), which displays, as text or figures, information from a battery indicator and a flow measuring instrument optionally installed on the inside of the body 1, is provided on the bottom 85 the body 1. A clip 88 is also provided for carrying.

Figure 9:
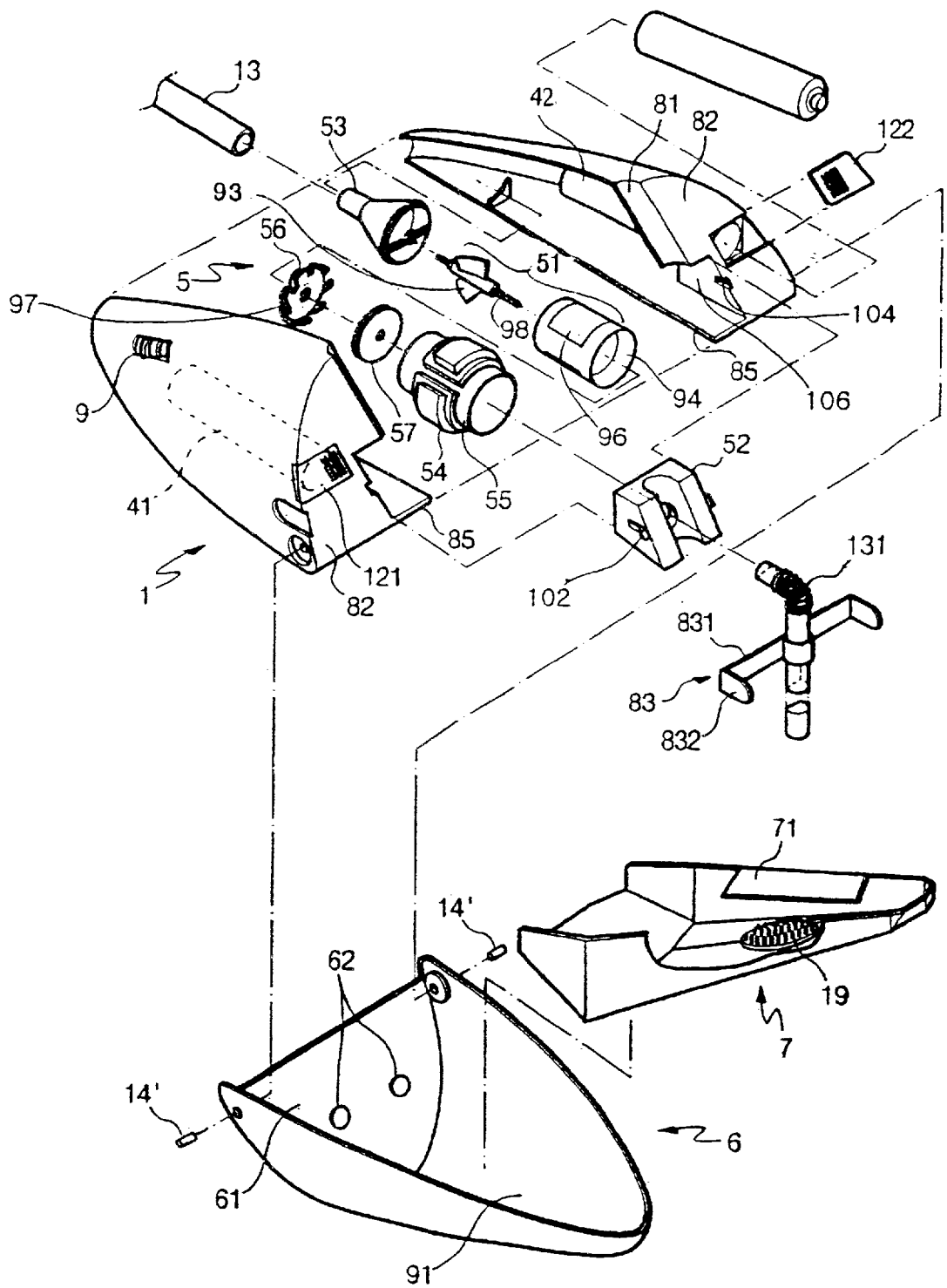
FIG. 9 is a exploded perspective view showing a condition of the separated urine discharge apparatus according to another embodiment of the present invention.

FIG. 9 depicts the second embodiment of the urine discharge apparatus according to the present invention in an exploded perspective view showing a condition of the separated apparatus, comprising the pump 5 for discharging the urine, the switch 9 for operating the pump 5, the body 1 containing the battery case 4 and the collection member 6 connected to the body 1 by the hinge pins 14'.

The collection member 6 has the form of a cone that is cut longitudinally with its cross section turned up. The bottom 85 of the collection member 6 is in the shape of sphere, thus allowing this member to be easily attached to perinaeum neum.

Both sides of the front wall 61 of the collection member 6 are connected to the outside of the rear wall 82 by pins 14'. Thus the collection member 6 is folded when being carried or stored and unfolded to a predetermined angle during use.

The disposable pack 7 inserted into the collection member 6 is kept and sold in a folded condition and unfolded during use so that the pack 7 may occupy the space for collecting the urine discharged from the urethra. Also the disposable pack 7 has a flange 71 extending longitudinally along the edge of the side walls so as to prevent the urine from spilling, and a non-woven fabric 19 is attached to the inside bottom of the disposable pack 7.

The body 1 has the same shape as the collection member 6 with the base having a curved surface and is formed to be inserted into the collection member 6 so as to minimize its volume when the urine discharge apparatus is stored or carried. Although the body 1 in FIG. 9 has a structure that is split longitudinally along the center line into two portions, this structure is not limited and may be formed such that the bottom 85 is split laterally.

The pump 5 which contains impeller 51 and has the inlet 52 and the outlet 53 on opposite sides is arranged longitudinally along the center line of the body 1. The inlet 52 of the pump 5 extends to the outside of the rear wall 82 and can be attached and detached from the pump 5. The introduction hose 131 is connected to the inlet 52 and the discharge hose 13 to the outlet 53. An end of the introduction hose 131 is fitted tightly in the inlet 52 of the pump 5 so as to prevent liquid from leaking, and the other end of introduction hose 131 extends to the inside of the collection member 6.

The introduction hose 131 is made of a synthetic resin and has a wrinkle at its central part so that the introduction hose 131 is flexible.

The discharge hose 13 is connected to the front end of the body 1 for discharging the urine outward and may be provided with a auxiliary hose 13' for facilitating urination of bedridden patients with the help of a nurse or for oneself. To this ends the discharge hose 13 is preferably made of hard synthetic resin.

The groove 81 is provided for containing the introduction hose 131 as the collection member 6 is folded upward, and is formed at the rear wall 82 of the body 1 so that the urine discharge apparatus can minimize its volume in being folded.

The switch 9 for supplying the pump 5 with power is mounted on one side of the body 1 according to the user and the receptacles 41 and 42 having doors 121 and 122 respectively are arranged inside of the body 1.

The hose clip 83 having blade portion 831 on both sides holds the introduction hose 131 extending to introduce the urine collected in the collection member 6. The hose clip 83 helps the end of the introduction hose 131 turn toward bottom of the collection member 6 while holding the disposable pack 7, and thus the urine collected in the collection member 6 is introduced to the plump 5 without detention.

The glide portion 932 of the hose clip 83 is provided so as to assure that the disposable pack 7 maintains the condition of being completely unfolded, and an auxiliary steel plate or wire may be combined to the guide portion 832. It is possible to modify the shape of the guide portion 832 if this modification promotes the restriction function of the guide portion 832.

Furthermore, the magnets 62 are provided on the front wall 61 of the collection member 6 so as to affix the metallic hose clip 83 combined with the introduction hose 131 to the front wall 61. Thereby encouraging the introduction hose 131 inserted in the hose clip 83 to follow the movement of the collection member 6 during rotation of the collection member 6.

The pump 5 installed in the body 1, as one embodiment, comprises a casing 55 with an electromagnet 54 wound as a coil around the casing 55, a cylindrical impeller 51 arranged inside of the casing 55, wherein a screw assembly is installed inside of the cylindrical impeller 51, a guide disc 56 having a plurality of flaps 97 on the outer circumference thereof for guiding a flow of the urine, and a centrifugal auxiliary impeller 57.

When the coil arranged around the outer surface of the casing 55 is supplied with electric power from the batteries through the switch 9, a single polarity occurs simultaneously at the electromagnet 54. The impeller 51 is repelled by the same polarity as the electromagnet 54 so that the impeller 51 rotates and discharges the urine. The construction of the pump 5 is not limiting, and any typical pump may be used if it can discharge the urine.

The impeller 51 includes a cylinder sleeve 94 having a diameter less than the casing 55, a magnet 96 with a North pole and a South pole filled in an outer circumference of the sleeve 94, the sleeve 94 to be rotated by the electromagnet 54, a rotating blade 93 fixed within the sleeve 94 by adhesion or other means for generating vacuum pressure to introduce urine into the impeller 51, and a shaft 98 attached to an axis of the rotating blade 93 to form a rotating center.

The pump 5 is preferably removable from the body 1 with the introduction hose 131 and discharge hose 13 so that it is possible to disinfect and replace the pump 5. Therefore, in order to remove the pump, a hole 106 is formed in the rear wall 82 and a groove 104 is formed along both inner walls of the hole 106. On both side walls of the inlet 52, hooks 102 are formed to be inserted into the grooves 104, respectively. Additionally, a typical system including a flow measuring instrument, a battery indicator and/or a timepiece may by optionally incorporated in the body 1, and a display 87 which shows information from the system as text or figures may be installed in the bottom 85 of the body 1. Such a system combined with the display 87 supplies the data necessary to remedy problems with the device.

The clip 88 is also provided on the bottom 85 for carrying the pump 5.

The method of using the above described embodiment of the urine discharge apparatus will now be described.

A battery is inserted into the receptacles 41 and 42 after the doors 121 and 122 arranged in the rear wall 82 are opened and the collection member 6 is adjusted to some angle that is convenient for urination. The pump 5 then rotates simultaneously upon urination or right before urination begins by moving the switch 9 to the ON position.

The urine discharged from the urethra is introduced to the introduction hose 131 by sucking operation of the pump 5 as soon as it is collected in the collection member 6, and continuously flows through the inlet 52 and impeller 51 to the outlet 53, and is discharged outward by ejection of the pump 5 through discharge hose 13.

After the urine collected in the collection member 6 is completely discharged, operation of the pump 5 comes to a halt by moving the switch 9 to the OFF position. Thus an operation cycle of the urine discharge apparatus is complete and the apparatus may be folded to be carried or stored.

Figure 10:
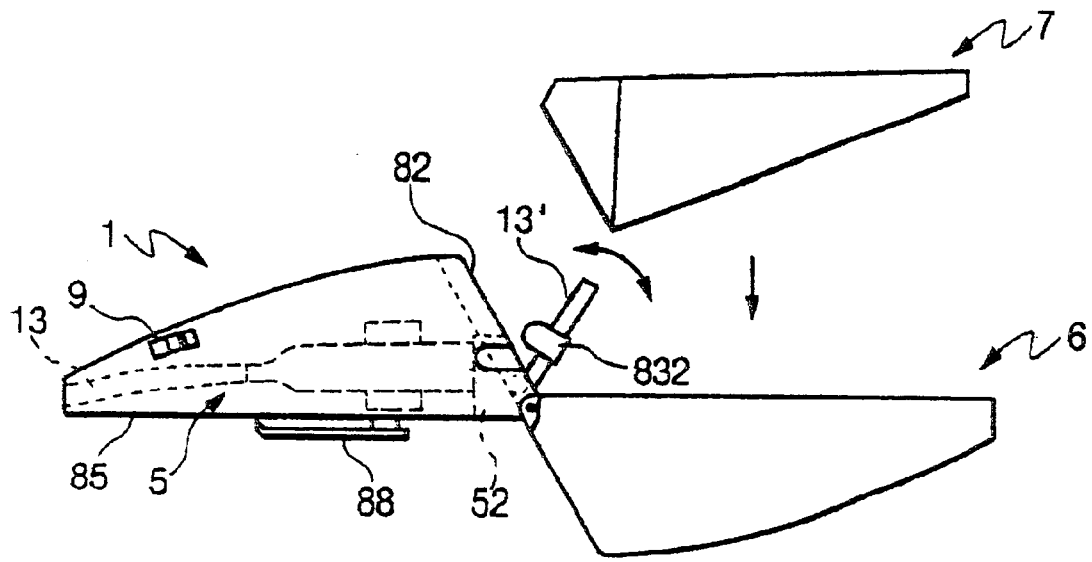
FIG. 10 and FIG. 11 show an operational condition of the urine discharge apparatus of FIG. 9.
Figure 11:
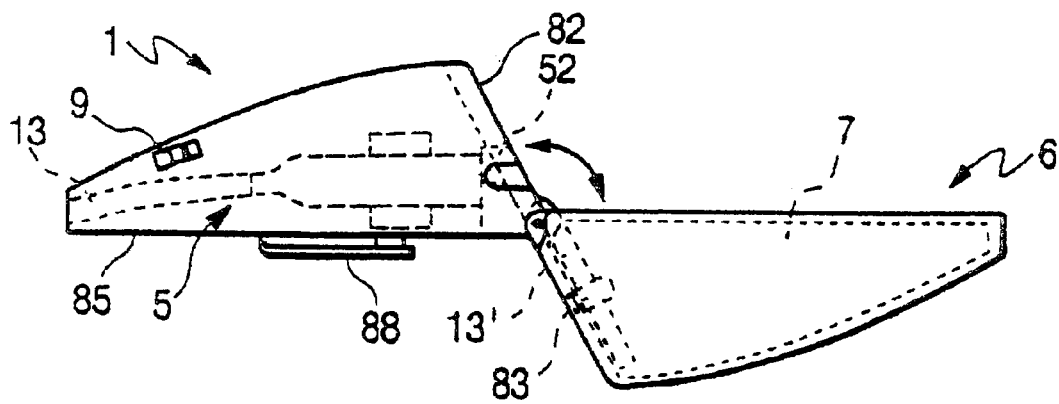
Figure 12:
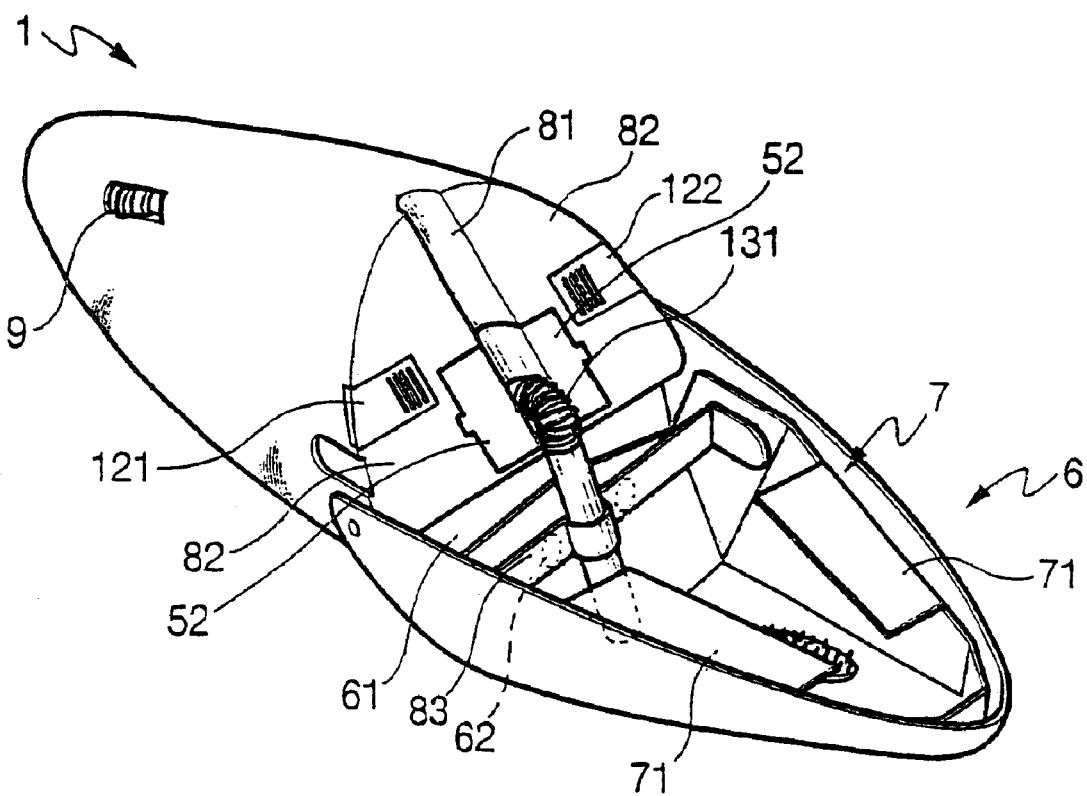
FIG. 12 is a perspective view showing a use condition of the urine discharge apparatus of FIG. 9.
Figure 13:
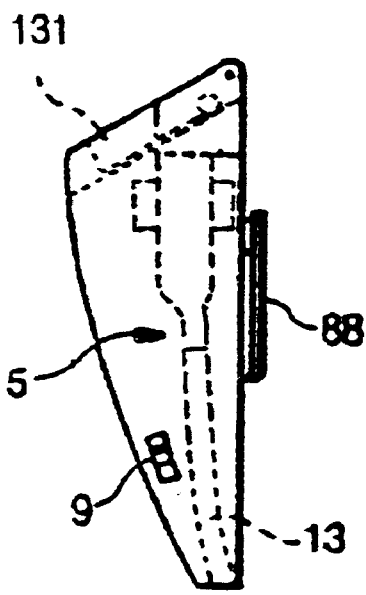
FIG. 13 is a side view of the urine discharge apparatus of the FIG. 9.
Figure 14:
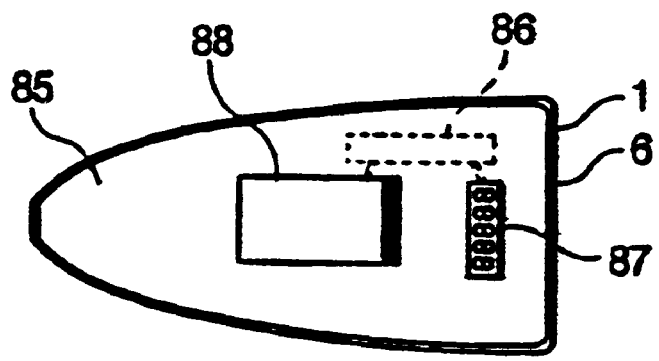
FIG. 14 is a bottom view of the urine discharge apparatus of FIG. 9.

When the disposable pack 7 is used as shown in FIGS. 10 and 11, the disposable pack 7 is tightly attached to the collection member 6 by magnetic force of the magnets 62. In this case, the urine can be absorbed in the non-woven fabric 19 without spreading. The flange 71 arranged along both sides in the rim of the disposable pack 7 further prevents the urine from spreading. Urine beyond the absorbability of the non-woven fabric 19 flows down to be collected in the lower portion of the disposable pack 7 The discharge process with the disposable pack 7 is more sanitary than without the disposable pack 7.

Also, since the system 86 provides information including the amount of urine, time to charge the battery and time, and this information is displayed on the display 87 arranged in the bottom 85 of the body 1 as text or figures, it is possible to effectively manage and use the apparatus with ease.

As previously mentioned, the apparatus according to the present invention is not only simple in construction but also easily adjusted to convenient angles for use, and can help protect the body from infection from toilet seats by use of the disposable pack 7.

Additionally, a disabled patient unable to get to the bathroom can urinate easily using this apparatus, and the urine discharge apparatus can provide advantages including that a user can examine oneself through the health index and check for pregnancy.

The apparatus is convenient to carry and store due to its small size in being folded, and provides the advantage that a user can detect a disease in the early stages by the analysis of the urine, thus enhancing medical efficiency.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

I claim:

1. A urine discharge apparatus for a female comprising:
    a collection member in the shape of a bucket;
    a pump member connected to the collection member by a hinge and including a pump, the pump open to the collection member so that the pump removes urine collected in the collection member and discharges the urine into an outlet thereof; and a driving member connected to the pump member and including a battery, the battery supplying electric power for operating the pump.

2. The urine discharge apparatus for a female of claim 1, wherein the driving member includes a battery case which is axially connected to a clip for receiving a battery upon rotation away from the driving member, a switch mounted on a top end of the driving member for turning on the electric power, and a door in an end portion of the driving member provided to open and close the entrance of the battery case by action of a spring.

3. The urine discharge apparatus for a female of claim 2, wherein the switch is an adjustable resistance switch for controlling rotation speed of the pump.

4. The urine discharge apparatus for a female of claim 1, wherein the driving member includes a through passage formed longitudinally in a bottom portion of the driving member such that a discharge hose extending from the outlet of the pump penetrates the driving member within the through passage.

5. The urine discharge apparatus for a female according to claim 4, further comprising an auxiliary hose connected to an end of the discharge hose such that the auxiliary hose protrudes outward from the driving member.

6. The urine discharge apparatus for a female of claim 1, wherein the collection member includes a disposable pack mounted on the collection member, the disposable pack having a flange on a side wall adapted for contacting the perinaeum neum.

7. The urine discharge apparatus for a female of claim 6, wherein a test paper is attached within the disposable pack for health and pregnancy testing.

8. The urine discharge apparatus for a female of claim 6, wherein a non-woven fabric is attached within the disposable pack for preventing urine from leaking.

9. The urine discharge apparatus for a female of claim 1, further comprising a discharge pipe coupled in the middle of a hinge for connecting the collection member and the pump member for introducing the urine collected in the collection member to an inlet of the pump and securing a disposable pack to a bottom surface of the collection member.

10. The urine discharge apparatus for a female of claim 1, wherein a float-type switch is provided within the collection member.

11. The urine discharge apparatus for a female according to claim 1, further comprising a cover for protecting the driving member and the pump member.

12. A urine discharge apparatus for a female comprising:
a hollow body;
a pump installed in the body and having an inlet and an outlet;
a switch mounted to the body for controlling a flow of current supplied to the pump;
an introduction hose connected to the inlet and positioned outside the body; and
a collection member connected to a rear wall of the body by a hinge and having a shape of a bucket.

13. The urine discharge apparatus for a female of claim 12, wherein the pump includes;
a cylindrical casing;
an electromagnet formed by winding a coil around the casing;
a cylindrical sleeve mounted in the casing separated from the casing by a predetermined space;
a magnet mounted in an outer circumference of the sleeve; and
a rotating blade mounted in the sleeve.

14. The urine discharge apparatus for a female of claim 13, wherein the pump includes a shaft mounted on an axis of the rotating blade and a guide disk is mounted to the shaft.

15. The urine discharge apparatus for a female of claim 14, wherein a plurality of equally spaced flaps protrude from an outer circumference of the guide disk.

16. The urine discharge apparatus for a female of claim 15, wherein the pump includes an auxiliary centrifugal impeller mounted to the shaft.

17. The urine discharge apparatus for a female of claim 15, further comprising a monitoring system including a flow measuring instrument for measuring a flow rate of urine, a battery indicator for indicating the remaining charge of a battery connected to the switch and a timepiece, wherein a display is installed in a bottom portion of the body for displaying information from the monitoring system as a text or figures.

18. The urine discharge apparatus for a female of claim 15, wherein a metallic hose clip is mounted to the introduction hose.

19. The urine discharge apparatus for a female of claim 18, wherein the collection member includes a magnet mounted within the collection member for removably mounting the hose clip thereto.

20. The urine discharge apparatus for a female of claim 14, wherein the pump includes n auxiliary centrifugal impeller mounted to the shaft.

21. The urine discharge apparatus for a female of claim 14, further comprising a monitoring system including a flow measuring instrument for measuring a flow rate of urine, a battery indicator for indicating the remaining charge of a battery connected to the switch and a timepiece, wherein a display is installed in a bottom portion of the body for displaying information from the monitoring system as a text or figures.

22. The urine discharge apparatus for a female of claim 14, wherein a metallic hose clip is mounted to the introduction hose.

23. The urine discharge apparatus for a female of claim 22, wherein the collection member includes a magnet mounted within the collection member for removably mounting the hose clip thereto.

24. The urine discharge apparatus for a female of claim 13, further comprising a monitoring system including a flow measuring instrument for measuring a flow rate of urine, a battery indicator for indicating the remaining charge of a battery connected to the switch and a timepiece, wherein a display is installed in a bottom portion of the body for displaying information from the monitoring system as text or figures.

25. The urine discharge apparatus for a female of claim 13, wherein a metallic hose clip is mounted to the introduction hose.

26. The urine discharge apparatus for a female of claim 25, wherein the collection member includes a magnet mounted within the collection member for removably mounting the hose clip thereto.

27. The urine discharge apparatus for a female of claim 12, wherein the body has an opening at a rear side thereof and the pump is removably mounted inside the opening.

28. The urine discharge apparatus for a female of claim 27, wherein a hook is formed at the opening of the body and a groove is formed inside of the opening for attaching and releasing the hook.

29. The urine discharge apparatus for a female of claim 12, wherein a clip is mounted to a lower surface of the body.

30. The urine discharge apparatus for a female of claim 12, further comprising a monitoring system including a flow measuring instrument for measuring a flow rate of urine, a battery indicator for indicating the remaining charge of a battery connected to the switch and a timepiece, wherein a display is installed in a bottom portion of the body for displaying information from the monitoring system as text or figures.

31. The urine discharge apparatus for a female of claim 12, wherein the collection member includes a disposable pack mounted in the collection member.

32. The urine discharge apparatus for a female of claim 31, wherein a non-woven fabric is attached within the disposable pack.

33. The urine discharge apparatus for a female of claim 32, wherein the disposable pack includes side walls, the side walls having a flange extending longitudinally along an edge of each side wall, the flange bending inwardly.

34. The urine discharge apparatus for a female of claim 12, wherein a metallic hose clip is mounted to the introduction hose.

35. The urine discharge apparatus for a female of claim 34, wherein the collection member includes a magnet mounted within the collection member for removably mounting the hose clip thereto.

* * * * *